(12) United States Patent
Bretton et al.

(10) Patent No.: US 6,454,802 B1
(45) Date of Patent: Sep. 24, 2002

(54) INTRAOCULAR LENS IMPLANT FOR THE PREVENTION OF SECONDARY CATARACTS

(75) Inventors: Randolph H. Bretton, Belleville, IL (US); David P. Vanderbilt; George F. Green, both of St. Louis, MO (US)

(73) Assignee: Bausch & Lomb Incorporated, Rochester, NY (US)

( * ) Notice: Subject to any disclaimer, the term of this patent is extended or adjusted under 35 U.S.C. 154(b) by 36 days.

(21) Appl. No.: 09/642,966

(22) Filed: Aug. 21, 2000

(51) Int. Cl.$^7$ ............................................. A61F 2/16
(52) U.S. Cl. .................................. 623/6.61; 623/6.62
(58) Field of Search .......................... 623/6.1, 6.16, 623/6.49, 6.5, 6.56, 6.59, 6.61, 6.62

(56) References Cited

U.S. PATENT DOCUMENTS

| | | | |
|---|---|---|---|
| 4,432,751 A | 2/1984 | Emery et al. | 604/49 |
| 4,515,794 A | 5/1985 | Emery et al. | 514/244 |
| 4,657,930 A | 4/1987 | Emery et al. | 514/557 |
| 4,664,666 A | * 5/1987 | Barrett | 623/6 |
| 4,822,358 A | 4/1989 | Jaffe | 623/6 |
| 4,842,600 A | 6/1989 | Feaster | 623/6 |
| 4,847,240 A | 7/1989 | Ryser et al. | 514/12 |
| 4,863,464 A | 9/1989 | Dusek | 623/6 |
| 4,871,350 A | 10/1989 | Lam et al. | 604/49 |
| 4,918,165 A | 4/1990 | Soll et al. | 530/391 |
| 4,936,850 A | 6/1990 | Barrett | 623/6 |
| 4,955,889 A | 9/1990 | Van Gent | 606/107 |
| 4,957,505 A | 9/1990 | McDonald | 623/6 |
| 5,002,571 A | * 3/1991 | O'Donnell, Jr. et al. | 623/6 |
| 5,055,291 A | 10/1991 | Lam et al. | 424/85.91 |
| 5,202,252 A | 4/1993 | Emery et al. | 435/240.27 |
| 5,273,751 A | 12/1993 | Dubroff | 424/427 |
| 5,620,013 A | * 4/1997 | Bretton | 128/898 |
| 6,106,554 A | * 8/2000 | Bretton | 623/6.62 |

* cited by examiner

Primary Examiner—Corrine McDermott
Assistant Examiner—Hieu Phan
(74) Attorney, Agent, or Firm—Rita D. Vacca

(57) ABSTRACT

A surface treated intraocular lens implant for use in the replacement of a cataractous natural lens to prevent posterior capsular opacification. The surface treated intraocular lens includes one or more proteins, polypeptides, polyamino acids or polyamines bound to the surface of the intraocular lens implant covalently, non-covalently or a combination thereof. The one or more proteins, polypeptides, polyamino acids or polyamines present on the surface of the intraocular lens implant serves to reduce or eliminate residual lens epithelial cell migration within the lens capsule. By preventing residual lens epithelial cell migration, posterior capsular opacification of the intraocular lens implant is thus reduced or eliminated.

18 Claims, No Drawings

INTRAOCULAR LENS IMPLANT FOR THE PREVENTION OF SECONDARY CATARACTS

FIELD OF THE INVENTION

The present invention relates to coated intraocular lens implants, methods for coating intraocular lens implants and a method of using coated intraocular lens implants to reduce or eliminate residual lens epithelial cell migration and posterior capsular opacification or secondary cataract formation following the extracapsular extraction of a cataractous lens. More particularly, the present invention is directed to coated intraocular lens implants that adhere to an interior surface of an aphakic eye's lens capsule to prevent residual lens epithelial cell migration.

BACKGROUND OF THE INVENTION

Cataract extraction is among the most commonly performed operations in the United States and the world. A cataractous lens is located within a capsular sac or lens capsule in the posterior chamber of the eye. In order to gain access to the cataractous lens, an incision typically is made at the limbus of the eye for the purpose of introducing a surgical instrument into the anterior chamber of the eye. In the case of extracapsular cataract extraction, a capsulorhexis procedure is performed in which a portion of the anterior membrane of the lens capsule adjacent to the iris is removed using a surgical cutting instrument to cut and/or tear the same in order to provide direct access to the cataractous lens from the anterior chamber. The diseased lens is then removed through various known methods, including phacoemulsification. Phacoemulsification is a procedure entailing the application of ultrasonic energy to the diseased lens in order to break the cataractous lens into small pieces that can be aspirated from the lens capsule. With the exception of the portion of the anterior membrane of the lens capsule removed during the capsulorhexis procedure, the lens capsule remains substantially intact throughout an extracapsular cataract extraction. Following removal of the cataractous lens, an artificial intraocular lens (IOL) implant is typically implanted within the lens capsule in order to mimic the refractive function of a healthy natural lens.

Although cataractous lens removal with IOL implant replacement provides significant benefits to most cataract patients, it is estimated that up to fifty percent (50%) of all patients who have IOL implants placed within the lens capsule will develop posterior capsular opacification (PCO) or secondary cataract within five years after surgery. PCO is caused by the deposition of cells and fibers on the IOL implant and especially on the posterior capsular membrane. The deposition of cells and fibers behind the IOL implant obstructs light passing through the IOL implant and obscures the patient's vision. Such cell deposits originate from two sources: (1) the proliferation of residual lens epithelial cells on the interior surface of the lens capsule after surgery; and (2) the accumulation of inflammatory cells and protein deposits on the IOL implant. Of these two sources, the major cause of PCO is the proliferation and migration of residual lens epithelial cells on the capsular membrane.

Ophthalmic surgeons, aware of the problems associated with residual lens epithelial cells, typically take considerable care in trying to remove all residual lens epithelial cells prior to implantation of an IOL implant. However, despite such efforts, a significant number of residual lens epithelial cells are typically left on the interior surface of the lens capsule. Residual lens epithelial cells are often left within the lens capsule due to their position within the lens capsule. The position of the cells on an interior surface within the lens capsule makes the same difficult to observe and difficult to reach. The most common treatment for PCO entails the application of laser energy to the posterior membrane of the lens capsule for the purpose of performing a capsulotomy on the opacified posterior capsule. However, the laser energy applied to the posterior membrane of the lens capsule is ordinarily directed through the IOL implant. Laser energy has the potential of possibly damaging the optical and/or structural characteristics of the IOL implant. The application of laser energy to the posterior membrane of the lens capsule by design results in the destruction of a portion of the lens capsule as well. The destruction of a portion of the lens capsule creates risks from exposure of tissues to the vitreous, possibly resulting in serious or irreparable damage to the eye, such as an increase in intraocular pressure, retinal detachment and cystoid macular edema. Accordingly, it is preferable to prevent the occurrence of PCO rather than attempt to treat it at a later date using laser energy.

Various procedures for the prevention of PCO have been suggested in recent years. Many such procedures have included the application of chemicals to the interior surface of the lens capsule in order to destroy residual lens epithelial cells. However, none of these procedures has proven to be particularly successful in the prevention of PCO due to the fact that it is extremely difficult to destroy residual lens epithelial cells without simultaneously destroying other cells within the eye, including the possible destruction of the corneal endothelium. Other procedures suggested for the prevention of PCO include the utilization of an IOL implant manufactured from a naturally tacky or sticky material. Such an IOL implant is used to prevent PCO by adhering the same via its tacky or sticky surface to an interior posterior surface of an eye's lens capsule. PCO is thus prevented by adhering the IOL implant to the interior surface of the lens capsule and preventing the migration of residual lens epithelial cells across the capsular membrane. However, this procedure has not proven to be particularly commercially successful due to numerous difficulties associated with implanting and manipulating a tacky or sticky IOL implant that has the tendency to adhere to itself as well as to surgical instrumentation.

Accordingly, a long felt need exists for a reliable and cost effective method of preventing posterior capsular opacification or secondary cataract in cataract patients having IOL implants.

BRIEF SUMMARY OF THE INVENTION

Posterior capsular opacification (PCO) is believed to result primarily from residual lens epithelial cells of the germinal layer. These cells eventually proliferate and migrate across an eye's lens capsule into the eye's optical zone. The coated intraocular lens (IOL) implant of the present invention promotes adhesion of the IOL implant to an interior surface of an eye's lens capsule to reduce or eliminate cellular migration across the lens capsule and IOL implant.

The preferred embodiment of the coated IOL implant of the present invention is an IOL implant having one or more protein, polypeptide, polyamino acid and/or polyamine agents covalently bound to the surface thereof. Once the coated IOL implant is implanted within an eye and in contact with the eye's lens capsule, the protein, polypeptide, polyamino acid and/or polyamine agent coating on the IOL implant binds to the tissue of the lens capsule to prevent migration of residual lens epithelial cells. The subject coated IOL implant as just described may be used as customary in the field of ophthalmology for the replacement of a natural lens such as a cataractous lens.

Accordingly, it is an object of the present invention to provide a coated IOL implant useful in the prevention of PCO.

Another object of the present invention is to provide a coated IOL implant useful in the prevention of PCO, which is reliable and cost effective.

Another object of the present invention is to provide an IOL implant protein, polypeptide, polyamino acid and/or polyamine agent coating for the prevention of PCO, which is effective on IOL implants manufactured from any one of a variety of materials.

Another object of the present invention is to provide a method of using a protein, polypeptide, polyamino acid and/or polyamine agent coated IOL implant to prevent PCO.

Still another object of the present invention is to provide a coated IOL implant effective in reducing or eliminating residual lens epithelial cell migration across the interior lens capsule and implant.

These and other objectives and advantages of the present invention, some of which are specifically described and others that are not, will become apparent from the detailed description, examples and claims that follow.

DETAILED DESCRIPTION OF THE INVENTION

The coated intraocular lens (IOL) implant of the present invention is intended to be implanted in an eye following extracapsular cataract extraction or removal of a previously implanted artificial lens to reduce or eliminate posterior capsular opacification (PCO) through adherence of the IOL implant to the lens capsule. By adhering the IOL implant to the lens capsule, residual lens epithelial cells are prevented from migrating along or across the surface of the lens capsule and from obscuring the optical zone. Thereby, PCO is prevented. The IOL implant of the present invention may be employed for this purpose in connection with any extracapsular cataract extraction procedure.

Extracapsular cataract extraction entails the formation of an incision through the eye in order to provide direct access to the anterior chamber of the eye. Although the necessary incision is usually formed at the limbus of the eye, it will be appreciated that alternative locations for this incision may be selected at the discretion of the surgeon. Following the formation of the incision, a surgical instrument is introduced though the incision into the anterior chamber of the eye. The instrument is then advanced though the anterior chamber such that a cutting surface thereof is in the eye's posterior chamber and in direct contact with the anterior surface of the lens capsule. A capsulorhexis procedure is then performed, wherein a portion of the anterior membrane of the lens capsule is excised in order to provide direct access to the cataractous lens. The cataractous lens is then removed from the lens capsule of the eye (aphakia). It will be appreciated that a variety of procedures can be used to remove the cataractous lens, including phacoemulsification and laser ablation. Upon removal of the cataractous lens from the lens capsule, an IOL implant is inserted into the now aphakic eye for the purpose of mimicking the refractive characteristics of a natural lens. IOL implants, such as that of the present invention, are often placed within the remaining portions of the lens capsule.

The subject IOL implant may be implanted in an aphakic eye to mimic the refractive characteristics of a healthy natural lens. Surgical methods of implanting an IOL implant in an aphakic eye are well known to those skilled in the art as described in U.S. Pat. Nos. 4,955,889 and 4,957,505 each incorporated herein in its entirety by reference.

The subject IOL implant of the present invention may be manufactured in any configuration acceptable to those skilled in the art for the intended purpose of replacing a natural lens. The IOL implant may be of a plate-style configuration as described in U.S. Pat. Nos. 4,664,666 and 4,936,850 each incorporated herein in its entirety by reference, or of a haptic-style configuration as described in U.S. Pat. Nos. 4,822,358, 4,842,600 and 4,863,464 each incorporated herein in its entirety by reference. Any suitable posterior chamber lens configuration is equally suitable for use in the present invention.

The IOL implant of the present invention may be formed from one or more of any number of acceptable materials known to those skilled in the art of IOL manufacture such as for example but not limited to polymethylmethacrylate (PMMA), acrylics, silicones, hydrogels or a combination thereof. However, for purposes of the present invention, hydrogel materials are preferred due to the ease of attaching a protein and/or polyamine agent thereto.

Once one or more suitable materials are selected for the manufacture of the subject IOL implants, one or more suitable protein, polypeptide, polyamino acid and/or polyamine agents are selected. The protein, polypeptide, polyamino acid and/or polyamine agents are selected to promote lens capsule adhesion and not self-adhesion (cohesion) or adhesion to surgical instruments and the like. The same is accomplished by selecting agents that are known to bind components of the lens capsule. The lens capsule is a basement membrane. The major components of basement membranes are type IV collagen, heparan sulfate proteoglycans and laminin. Fibronectin is thought to bind basement membranes under some conditions. Each component of the basement membrane binds to at least one other component comprising the basement membrane. Accordingly, attaching one of the components comprising the basement membrane to the surface of an IOL will provide a linking agent from the IOL to the lens capsule membrane. In addition, some polyamines or polyamino acids, such as polyethyleneimine and polylysine are known to bind to heparin and heparan sulfate. Therefor, polyethyleneimine and polylysine are excellent binding agents as they are inexpensive and easy to manufacture in different molecular weights. The one or more protein, polypeptide, polyamino acid or polyamine agents may be attached directly to the surface of an already formed IOL implant using covalent bonding. In such a case, the one or more coating agents are covalently bound to the IOL implant's surface using wet chemical techniques, photochemical techniques, plasma techniques or gamma irradiation, including E-beam. Alternatively, the protein, polypeptide, polyamino acid and/or polyamine agent may be mixed with the selected material monomers or comonomers and polymerized for implant manufacture.

Suitable protein, polypeptide, polyamino acid or polyamine agents for use in accordance with the present invention include for example, but are not limited to polyethyleneimine, poly-L-lysine, poly-D-lysine, fibronectin, laminin, type I, II, III and IV collagen, thrombospondin, vitronectin, polyarginine, platelet factor IV and polypeptide fragments of the proteins noted, but preferably poly-L-lysine and polyethyleneimine due to ready availability and relatively low cost. For purposes of simplicity, each poly-L-lysine and poly-D-lysine is hereinafter referred to indiscriminately as "polylysine".

The coated IOL implants of the present invention having one or more protein or polyamine agents covalently bound to the surface thereof may be packaged and sterilized using methods known to those skilled in the art. The preferred methods of making the subject IOL implants for the prevention of PCO are described in still greater detail in the examples that follow.

EXAMPLES

Example 1

Poly(2-hydroxyethyl methacrylate-co-6-hydroxyhexyl methacrylate)/Polylysine

IOLs of 18-wt % water content made from 2-hydroxyethyl methacrylate (HEMA) (70 mol %) and 6-hydroxyhexyl methacrylate (HOHEXMA) (30 mol %), known commercially as Hydroview® IOLs, were used as the coating substrate in the present example. Three IOLs were added to a glass vial containing 5 mL of a solution of 0.0069-g of poly(L-lysine).HBr (Sigma P-1524) dissolved in 0.1 M $Na_2CO_3$. For controls, three Hydroview IOLs were added to a vial containing 5 mL of deionized (DI) water. The vials were autoclaved for one hour at 121° C. After cooling, the IOLs were copiously rinsed with DI water and stored in DI water.

To simulate binding to a heparin or heparan sulfate containing macomalecular structure such as a lens capsule, a slurry of heparin-coated sepharose beads (Pharmacia Biotech AB, 5-4836) was prepared by dispersing a 1 mL syringe of beads in 100 mL of phosphate buffered saline (PBS). To two 50-mL polypropylene centrifuge tubes were added 2-mL of the bead suspension, a test IOL and a control IOL. The tubes were shaken with the IOLs and then allowed to stand overnight. The IOLs were carefully removed from the tubes and gently swirled in a beaker containing balanced salt solution (BSS). The IOLs were examined by microscopy for the presence/absence of attached beads. The polylysine-coated IOLs had a high density of attached heparin/sepharose beads while the control IOLs had no attached beads.

Example 2

Poly(HEMA-co-HOHEXMA)/Polyethyleneimine

Hydroview IOLs were similarly coated using solutions of polyethyleneimine (Sigma P-3143) in DI water (0.0111-g 50% PEI/5 mL) and 0.1 M $Na_2CO_3$ (0.0100-g 50% PEI/5 mL). Both samples were found to bind heparin-coated sepharose beads per Example 1.

Example 3

Evaluation in a Porcine Lens Capsule

Hydroview IOLs were similarly coated (3 per vial) with poly(L-lysine) HBr and PEI using solutions of 0.0051-g polylysine in 5 mL of 0.025 M $NaHCO_3$/0.025M $Na_2CO_3.H_2O$ and 0.0098-g of 50% PEI in 5 mL of the same buffer. Two examples of each coated IOL and two uncoated controls were placed inside the empty capsular bags of porcine cadaver eyes and the eyes were refrigerated over a weekend. After warming the globes to room temperature, the relative attachment strength was assessed by tugging on the haptics of each IOL. The control IOLs and PEI-coated IOLs were easily separated from porcine tissue. One of the polylysine IOLs indicated some attachment that was overcome by tugging. The second polylysine-coated IOL was more firmly attached to the tissue and required a considerable effort to free it from the lens capsule tissue.

In a previous trial, Hydroview IOLs coated with PEI in the same manner described above exhibited considerable resistance to removal from porcine capsular bags.

Example 4

Poly(HEMA co-HOHEXMA-co-GMA)/Polylysine

IOL polymer substrates were made containing 1-mol % and 2-mol % glycidyl methacrylate (GMA) to provide additional sites for covalent attachment of the coating polymer via reaction of the amino and epoxy functionalities. Lathe cut disks were coated with a 1%-w/w solution of polylysine in 50:50 carbonate/bicarbonate buffer by autoclaving for one hour at 121° C. The washed disks were exposed to heparin/sepharose beads as described previously. The beads were found to cling to the coated disks in high density. The binding was found to be very strong but not covalent. This is evident from the observation that in most cases, the beads were still present after exposure to 2 M NaCl, but not after exposure to 4 M guanidine.

As described above, the coated IOL implants of the present invention provide an effective method of preventing PCO in patients in which the implants are used. The IOL implants have a tack-free surface. The IOL implants do not adhere to themselves when folded or manipulated or to surgical instrumentation during implantation. The subject IOL implants when implanted in a lens capsule of an aphakic eye, adhere to the lens capsule by means of its protein or polyamine agent coating to prevent residual lens epithelial cell migration and thus PCO. The present description of the subject IOL implants, the methods of making the same and the method of using the same are provided herein for purposes of illustration and explanation. It will be apparent to those skilled in the art that modifications and changes may be made to the preferred embodiments described herein without departing from the scope and spirit thereof.

We claim:

1. An intraocular lens implant comprising:
   an intraocular lens implant; and
   one or more proteins, polypeptides, polyamino acids or polyamines covalently bound to the surface of said implant using wet chemical, photochemical, plasma, gamma irradiation or polymerization techniques to form a tack-free surface;
   whereby said one or more proteins, polypeptides, polyamino acids or polyamines adhere said implant to an interior posterior surface of an aphakic eye's lens capsule upon contact therewith.

2. The intraocular lens implant of claim 1 wherein said implant is manufactured from one or more materials selected from the group consisting of polymethylmethacrylate, silicone, acrylate and hydrogel.

3. The intraocular lens implant of claim 1 wherein said implant is manufactured from a hydrogel material.

4. The intraocular lens implant of claim 1 wherein said implant is manufactured in a plate configuration or a haptic configuration.

5. The intraocular lens implant of claim 1 wherein said one or more proteins are selected from the group consisting of fibronectin, laminin, type I, II, III or IV collagen, thrombospondin, vitronectin, platelet factor IV and polypeptide fragments thereof.

6. The intraocular lens implant of claim 1 wherein said one or more polyamines or polyamino acids are selected from the group consisting of polyethyleneimine, polyarginine, poly-L-lysine and poly-D-lysine.

7. A method of manufacturing an intraocular lens implant comprising:

fabricating an intraocular lens implant; and covalently binding one or more proteins, polypeptides, polyamino acids or polyamines to the surface of said implant using wet chemical, photochemical, plasma, gamma irradiation or polymerization techniques to form a tack-free surface;

whereby said one or more proteins, polypeptides, polyamino acids or polyamines adhere said implant to an interior posterior surface of an aphakic eye's lens capsule upon contact therewith.

8. The method of claim 7 wherein said implant is manufactured from one or more materials selected from the group consisting of polymethylmethacrylate, silicone, acrylate and hydrogel.

9. The method of claim 7 wherein said implant is manufactured from a hydrogel material.

10. The method of claim 7 wherein said implant is manufactured in a plate configuration or a haptic configuration.

11. The method of claim 7 wherein said one or more proteins are selected from the group consisting of fibronectin, laminin, type I, II, III or IV collagen, thrombospondin, vitronectin, platelet factor IV and polypeptide fragments thereof.

12. The method of claim 7 wherein said one or more polyamines or polyamino acids are selected from the group consisting of polyethyleneimine, polyarginine, poly-L-lysine and poly-D-lysine.

13. A method of implanting an intraocular implant within an eye comprising:

creating an incision in an eye;

removing a diseased natural lens from said eye;

implanting said implant, covalently bound with one or more proteins, polypeptides, polyamino acids or polyamines using wet chemical, photochemical, plasma, gamma irradiation or polymerization techniques to form a tack-free surface, within said eye's lens capsule; and closing said incision;

whereby said one or more proteins, polypeptides, polyamino acids or polyamines adhere said implant to an interior posterior surface of said eye's lens capsule upon contact therewith.

14. The method of claim 13 wherein said implant is manufactured from one or more materials selected from the group consisting of polymethylmethacrylate, silicone, acrylate and hydrogel.

15. The method of claim 13 wherein said implant is manufactured from a hydrogel material.

16. The method of claim 13 wherein said implant is manufactured in a plate configuration or a haptic configuration.

17. The method of claim 13 wherein said one or more proteins are selected from the group consisting of fibronectin, laminin, type I, II, III or IV collagen, thrombospondin, vitronectin, platelet factor IV and polypeptide fragments thereof.

18. The method of claim 13 wherein said one or more polyamines or polyamino acids are selected from the group consisting of polyethyleneimine, polyarginine, poly-L-lysine and poly-D-lysine.

* * * * *